United States Patent

Naarmann et al.

[11] 4,386,203
[45] May 31, 1983

[54] HALOGEN-CONTAINING S-TRIAZINES

[75] Inventors: Herbert Naarmann, Wattenheim; Klaus Penzien, Frankenthal; Franz Brandstetter, Neustadt; Gerhard Lindenschmidt, Leimen; Erhard Seiler, Ludwigshafen, all of Fed. Rep. of Germany

[73] Assignee: BASF Aktiengesellschaft, Fed. Rep. of Germany

[21] Appl. No.: 305,857

[22] Filed: Sep. 25, 1981

[30] Foreign Application Priority Data

Oct. 16, 1980 [DE] Fed. Rep. of Germany ....... 3039059

[51] Int. Cl.³ ................. C07D 251/30; C07D 251/34
[52] U.S. Cl. .................................................. 544/219
[58] Field of Search ......................................... 544/219

[56] References Cited

U.S. PATENT DOCUMENTS

| | | | |
|---|---|---|---|
| 3,843,650 | 10/1974 | Pews et al. | 260/248 CS |
| 3,962,241 | 6/1976 | Hunter | 260/249.5 |
| 4,069,380 | 1/1978 | Eaton et al. | 544/212 |
| 4,142,048 | 2/1979 | Kappler et al. | 544/219 |
| 4,147,659 | 4/1979 | De Jonge et al. | 544/219 |
| 4,187,377 | 2/1980 | Narisawa et al. | 544/219 |

FOREIGN PATENT DOCUMENTS

| | | |
|---|---|---|
| 2641953 | 4/1977 | Fed. Rep. of Germany . |
| 1566675 | 7/1978 | France . |
| 55-25232 | 6/1980 | Japan . |
| 56-57771 | 5/1981 | Japan . |
| 1237256 | 6/1971 | United Kingdom . |
| 1331560 | 9/1973 | United Kingdom . |

Primary Examiner—John M. Ford
Attorney, Agent, or Firm—Keil & Witherspoon

[57] ABSTRACT

Halogen-containing s-triazine compounds of the formula I

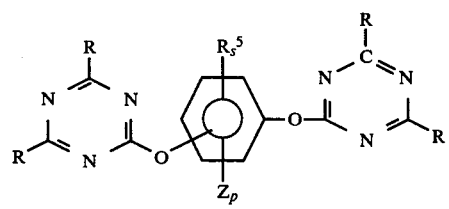

where R is OH, $R^1$, $R^2$ or $R^3$, $R^1$ is

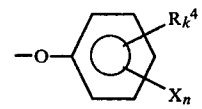

where $R^4$ is lower alkyl or lower haloalkyl, X is bromine or chlorine, k and n are 0 or integers from 1 to 5 and k+n is not more than 5, $R^2$ is

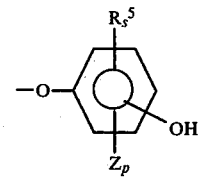

where $R^5$ is lower alkyl or lower haloalkyl, Z is bromine or chlorine, s and p are 0 or integers from 1 to 4 and s+p is not more than 4, and $R^3$ is

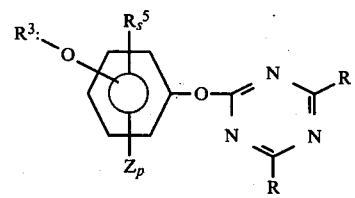

where R, $R^5$, Z, s and p have the above meanings.

The compounds claimed are prepared by reacting cyanuric chloride with a phenol of the formula III

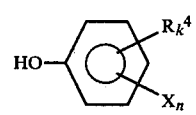

and a benzene derivative of the formula IV

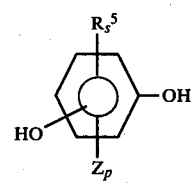

in the presence of a base.

The products thereby obtained are used for flameproofing thermoplastics, in particular styrene/acrylonitrile copolymers made impact-resistant with rubber (ABS resins).

3 Claims, No Drawings

HALOGEN-CONTAINING S-TRIAZINES

The present invention relates to halogen-containing s-triazines with two or more s-triazine rings. The compounds are prepared by reacting cyanuric chloride with a phenol and a benzene derivative containing 2 OH groups in the presence of an aqueous base, using a polar solvent. The compounds claimed are used for flameproofing thermoplastics.

The prior art includes:
1. French Pat. No. 1,566,675
2. U.S. Pat. No. 3,843,650
3. Japanese Published Application No. 25,232/1972
4. U.S. Pat. No. 4,187,377

(1) discloses halogen-containing s-triazines with one s-triazine ring. Tris-(2,4,6-tribromophenoxy)-s-triazine is described in (1), (2) and (3), and its use as a flameproofing agent for polyolefins, polystyrenes, ABS, PVC and the like is disclosed in (2) and (3). These tris-(polyhalophenoxy)-s-triazines have a good ignition-delaying action, but are not sufficiently stable to heat and give rise to exudation when mixed with synthetic resins. (4) furthermore discloses that polynuclear triazine compounds can be prepared from cyanuric chloride, phenols and bisphenols. The preferred compound bisphenol A, which is readily accessible and can easily be brominated, contains two phenyl rings which are linked via —$C(CH_3)_2$—. This aliphatic group, which is introduced to link the aromatic radicals and is readily combustible is of no effect or advantage when the known halo-s-triazines are used as flameproofing agents.

It is an object of the present invention to propose compounds containing simpler s-triazine systems and to develop a process for their preparation, which, starting from cyanuric chloride and halogenated phenols, gives s-triazines which essentially contain no readily combustible groups in the molecule, and have a substantial halogen content.

We have found that this object is achieved by s-triazines of the general formula I as claimed in the claim. These compounds are prepared from cyanuric chloride, phenols (III) and di-hydroxy-substituted benzene derivatives (IV) in the presence of a base.

The present invention accordingly relates to halogen-containing s-triazines as claimed in the claim.

The compounds of the formula I according to the invention or mixtures of compounds of the formula I with the corresponding tris-(polyhalophenoxy)-s-triazine compounds of the formula II

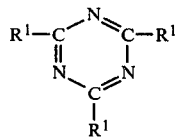

where $R^1$ has the meaning given in the claim can be prepared using phenols of the general formula III

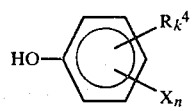

Suitable phenols for the reaction are the halophenols, for example monobromophenol, monochlorophenol, dibromophenol, dichlorophenol, tribromophenol, trichlorophenol, pentabromophenol, pentachlorophenol, cresol, monobromocresol, monochlorocresol, dibromocresol, dichlorocresol, tribromoresol and trichlorocresol, and the haloalkylphenols, for example (2-bromoethyl)-dibromophenol, (2-chloroethyl)-dichlorophenol and the like. Tribromophenol, trichlorophenol, pentabromophenol and pentachlorophenol are the preferred halophenols. Mixtures of two or more of the phenols mentioned can also be used for the preparation of the compounds I or of mixtures thereof with compounds II.

Tetrabromohydroquinone, tetrabromopyrocatechol and tetrabromoresorcinol are particularly suitable dihydroxy-substituted benzene derivatives of the general formula IV.

The halogen-containing s-triazines according to the invention are prepared by reacting a halophenol of the general formula III with a di-hydroxy-substituted benzene derivative of the general formula IV and with cyanuric chloride in the presence of a base, and preferably in the presence of a polar organic solvent, at from 0° to 100° C. The alkali metal or alkaline earth metal hydroxides, for example sodium hydroxide, potassium hydroxide or calcium hydroxide, or the alkali metal or alkaline earth metal carbonates, are used as acid acceptors in this reaction. An aqueous solution of sodium hydroxide is particularly preferred.

Polar organic solvents, such as halohydrocarbons, and especially ethers, cyclic ethers, ketones, esters and alcohols, are preferably used for the reaction. Cyclic ethers, for example 1,4-dioxane or tetrahydrofuran, are particularly preferred.

In reacting the reactants cyanuric chloride, and phenol of the formula III and the benzene derivative of the formula IV, the batch composition is preferably such that the number of hydroxyl equivalents from the phenol of the general formula III and the dihydroxy-substituted benzene derivative of the general formula IV equals the number of chlorine equivalents in the cyanuric chloride. Accordingly, if 1 mole of cyanuric chloride is used, 3 moles of alkali metal hydroxide solution are required. In a preferred embodiment for the preparation of the halogen-containing s-triazines according to the invention, the cyanuric chloride, the phenol of the formula III and the benzene derivative, containing 2 OH groups, of the general formula IV are introduced into tetrahydrofuran in the reaction vessel. The calculated amount of aqueous sodium hydroxide solution required is then added at from 20° to 50° C. The reaction is brought to completion by stirring under reflux for some hours. During working up of the reaction mixture, it is essential that the sodium chloride formed is removed. This is effected in a simple manner by stirring the reaction mixture into an excess of water or of a methanol/water mixture. The halogenated s-triazine is then isolated by filtration and dried. One embodiment of working up the reaction product comprises distilling off the water-miscible solvent after the reaction and taking up the residue in a chlorohydrocarbon, as the solvent. The suspension thereby formed is washed with water and the organic phase is separated off from the aqueous phase and evaporated. The halogenated s-triazines are thereby obtained as relatively low-viscosity, colorless to yellow melts. In another embodiment of the preparation of the compounds according to the invention, mixtures of chlorohydrocarbons and water are used as the reaction mixture, in which case it is advantageous to add phase transfer catalysts. The sequence in which the reactants are added is critical inasmuch as in water the chlorine in cyanuric chloride is replaced by OH groups, especially in an alkaline medium. Measures to suppress this less desirable side reaction, which leads to halogenated s-triazines with an increased OH number, consist in either adding the cyanuric chloride only after the remaining reactants have been introduced into the vessel, or adding the alkali only after all the other reactants have been introduced. Relatively high reaction temperatures are also to be avoided, especially at the start of the reaction.

The properties of the s-triazines according to the invention are determined by the molar ratio of cyanuric chloride (a) to di-hyroxy-substituted benzene derivative (c) of the general formula IV used during their preparation. This molar ratio must be from 1 to 20, preferably from 2 to 8. If a low molar ratio, of from 1 to 2, is used, the reaction products are crosslinked or high-melting, and with a molar ratio greater than from 8, and up to 20, the reaction products chiefly contain the tris(phenoxy)-triazine compound of the general formula II. If the molar ratio is greater than 2 and up to 8, molecular weight determinations show that the reaction products chiefly consist of a mixture of the s-triazine of the formula II and a halogenated s-triazine with 2 triazine nuclei, of the general formula I.

The compounds and mixtures of compounds according to the invention are preferably used for flameproofing thermoplastics. We have found that if sufficient halogen is present, in particular if the bromine content of the s-triazine and therefore of the plastic is sufficient, adequate flameproofing in accordance with the Underwriter Laboratories specifications is achieved for classification of the plastics into one of the burning classes 94 VE-0, 94 VE-1 or 94 VE-2 when tested in the vertical burning test. The conventional synergists, for example $Sb_2O_3$, $SnO_2$, $Fe_2O_3$ and the like, are preferably used, in the amounts known to the skilled worker, together with the flameproofing agent.

Thermoplastics suitable for flameproofing include polyethylene, polypropylene, polyisobutylene, polystyrene, styrene/acrylonitrile copolymers, polyamides and polyesters. High-impact thermoplastics, such as high-impact polystyrene, and styrene/acrylonitrile copolymers made impact-resistant with rubber (ABS resins) and, of the polyesters, polybutylene terephthalate, are particularly preferred. The flameproofing agents are used in amounts of from 2 to 25 parts by weight per 100 parts of the thermoplastic. The synergists are as a rule effective in amounts of from 1 to 10 parts by weight per 100 parts by weight of thermoplastic.

In addition to the flameproofing agent and synergists, the thermoplastics to be flameproofed can also contain the conventional additives, such as stabilizers, fillers, colored pigments, lubricants, plasticizers, antistatic agents or blowing agents, in the usual amounts known to the skilled worker. The flameproofing agent, the synergist and any additives used are incorporated by suitable, conventional mixing methods, for example in extruders, kneaders or mills. In particular, it is also possible to prepare a masterbatch of the flameproofing agent and synergist in the desired thermoplastic.

We have found that flameproofing agent mixtures containing more than 53% by weight of tris(tribromophenoxy)-s-triazine of the general formula II causes migration problems in ABS polymers.

The percentage contents of tris(tribromophenoxy)-s-triazine (formula II) in the brominated s-triazine mixture can be calculated, with certain assumptions, from the following equation:

$$\text{\% content of compound of the formula II} = \frac{(M-2) \cdot 100 \cdot 1068}{(M-2) \cdot 1068 + 1900}$$

In this equation, M is the molar ratio (a:c) of cyanuric chloride to tetrabromohydroquinone, which is especially used as a representative compound of the general formula IV. Molecular weight determinations of the reaction mixture show that this equation applies, with good approximation, for $M \geq 2$ when sodium tribromophenate is used as a further reactant.

In this sense, the ranges claimed are also to be regarded as approximate.

In the flameproofing of ABS resins, particularly good mechanical properties, of the molding materials coupled with freedom from migration, can be achieved if the halogen-containing s-triazines of the general formulae I and II according to the invention are used as a mixture containing from 22 to 53% by weight of a compound of the general formula II, based on the sum of the compound I and II; the % contents of II are calculated from the approximation formula in the penultimate paragraph for $M=a/c=2.5$ to $M=a/c=4$.

An ABS which contained 24 parts by weight of polybutadiene and had a matrix with an intrinsic viscosity of 55 or 80 was flameproofed with the s-triazines according to the invention. The viscosity number was determined by the method of DIN 53,726; 0.5 g of material were dissolved in 100 ml of dimethylformamide for this determination. The styrene content of the matrix was 65% by weight and the acrylonitrile content was 35% by weight.

5 parts by weight of a synergist (antimony trioxide) and 20 parts by weight of a flameproofing agent according to the present invention were mixed with the thermoplastic ABS polymer in a twin-screw extruder.

To test the mechanical properties of the ABS containing the flameproofing agent according to the invention, circular discs 2 mm thick were produced at 250° C. on an Arberg Allrounder 200 injection-molding machine. The damaging energy was determined by the method of DIN 53,443, sheet 1.

Pressed sheets $100 \times 100 \times 2$ mm were produced at 230° C. in order to test for the formation of surface films on articles molded from the molding materials according to the invention. The heating-up time was 3 minutes and the pressing time was 8 minutes at 230° C. The pressed sheets were kept at 60° C. in a drying oven. After certain intervals of time, they were examined visually to ascertain whether or not a surface film had formed.

Polybutylene terephthalate having a relative viscosity $\eta_{rel}$ of 1.67 (measured at a 0.5% strength solution in a 60/40 mixture of phenol and o-dichlorobenzene at 25° C.) were melted in a twin-screw extruder together with 10% by weight, based on the polymer, of the brominated triazine compounds, which contained not more than 70% by weight of tris(tribromophenoxy)-s-triazine, and 6% by weight, based on the polymer, of antimony trioxide as a flameproofing synergist. 30% by weight, based on the total mixture, of glass fibers were incorporated into the melt. The homogeneous mixture was discharged, cooled and granulated. Bars ⅛ and 1/16" thick were obtained from the granules by injection-molding and were tested in accordance with UL 94. The product is classifiable in burning class V of UL 94. Pairs of test bars were kept at 170° C. in a circulating air drying cabinet for 1, 3 and 7 days respectively. A slight deepening of color from light ivory to light beige was found. No surface film was detected. When tested in accordance with the German Central Telecommunications Laboratory Draft Standard 547 PV 1 of June 1971, the products showed no contact damage within the low-voltage range.

The Example and Comparison Experiments illustrate the invention. Unless otherwise indicated, the parts and percentages given in the Examples are by weight (cf. Table 2, which also contains the results of Comparative Experiments A to D).

EXAMPLES 1-8

0.2 mole of cyanuric chloride, x moles of tetrabromohydroquinone and y moles of tribromophenol are introduced into 400 ml of tetrahydrofuran in a glass flask. 24.8 g of NaOH, as an aqueous solution of about 50% strength, are then run in at 5°-10° C., and the mixture is stirred at room temperature and then refluxed for 6 hours. The solid is filtered off and a precipitate is obtained from the filtrate with 5 liters of methanol, washed with water and dried at 70° C. under reduced pressure. 130-170 g of halogenated s-triazine are obtained as a white solid.

EXAMPLE 9

0.2 mole of cyanuric chloride, 0.04 mole of tetrabromohydroquinone and 0.52 mole of tribromophenol are introduced into 400 ml of tetrahydrofuran in a glass flask. 24.8 g of sodium hydroxide, as an aqueous solution of about 50% strength, are then run in at +10° C. and the mixture is subsequently stirred at room temperature for 18 hours. The tetrahydrofuran is then distilled off and the residue is taken up in 500 ml of 1,2-dichloroethane. The organic phase is washed with 3 times 100 ml of water, and the solvent is distilled off. 190 g of a product melt, with a bromine content of 67.5%, remain.

EXAMPLES 10 TO 12 AND COMPARATIVE EXPERIMENTS A TO D

Flameproofing of ABS (cf. Table 2) with mixtures of compounds of the formulae I and II.

TABLE 1

| Example | Molar ratio of cyanuric chloride to tetrabromohydroquinone | $(x)^1$ moles of tetrabromohydroquinone | $(y)^1$ moles of tribromophenol | End product % bromine | End product molecular weight[2] |
|---|---|---|---|---|---|
| 1 | 2.0 | 0.1 | 0.4 | 67.2 | 1,980 |
| 2 | 2.22 | 0.09 | 0.42 | 67.0 | 1,920 |
| 3 | 2.5 | 0.08 | 0.44 | 66.8 | 1,780 |
| 4 | 3 | 0.066 | 0.466 | 66.9 | 1,520 |
| 5 | 4 | 0.05 | 0.50 | 67.0 | 1,510 |
| 6 | 5 | 0.04 | 0.52 | 67.1 | 1,140 |
| 7 | 7 | 0.028 | 0.54 | 66.9 | 1,250 |
| 8 | 8 | 0.025 | 0.55 | 66.8 | 1,320 |

[1] $2(x) + (y) = 0.2 \cdot 3$
[2] Mechrolab, chloroform as the solvent, extrapolated to zero concentration

TABLE 2

| Example | Flameproofing agent from Table 1 (parts by weight) | Antimony trioxide (parts by weight) | ABS (parts by weight) | Damaging energy (Nm) | Formation of surface film after 800 hours | Burning class |
|---|---|---|---|---|---|---|
| (According to the invention) | | | | | | |
| 10 | 3    20.0 | 5 | 75 | 12 | negative | VE-O |
| 11 | 4    20.0 | 5 | 75 | 16 | negative | VE-O |
| 12 | 5    20.0 | 5 | 75 | 19 | negative | VE-O |
| Comparative Experiments (Not according to the invention) | | | | | | |
| A | 1    20.0 | 5 | 75 | 0.5 | negative | VE-O |
| B | 2    20.0 | 5 | 75 | 7 | negative | VE-O |
| C | 6    20.0 | 5 | 75 | 20 | positive | VE-O |
| D | 7    20.0 | 5 | 75 | 20 | positive | VE-O |

We claim:
1. A halogen-containing s-triazine compound of the formula I

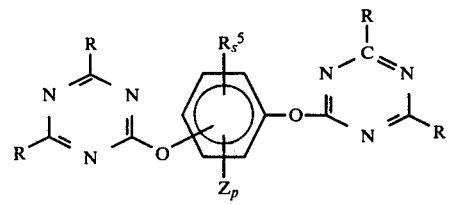

where R is OH, $R^1$, $R^2$ or $R^3$, $R^1$ is

where $R^4$ is lower alkyl or lower haloalkyl, X is bromine or chlorine, k and n are 0 or integers from 1 to 5 and $k+n$ is not more than 5, $R^2$ is

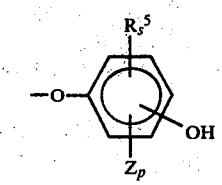
where $R^5$ is lower alkyl or lower haloalkyl, Z is bromine or chlorine, s and p are 0 or integers from 1 to 4 and s+p is not more than 4, and $R^3$ is
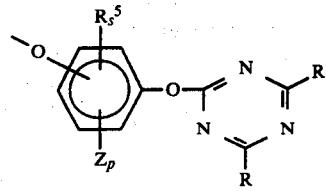
where R, $R^5$, Z, s and p have the above meanings.
2. A compound as defined in claim 1, wherein Z is bromine and wherein p is the integer 4.
3. A compound as defined in claim 1, wherein X is chlorine or bromine and wherein n is an integer of from 1 to 3 or 5.
* * * * *